(12) United States Patent  
Rubin et al.

(10) Patent No.: US 6,581,593 B1  
(45) Date of Patent: Jun. 24, 2003

(54) UNIVERSAL OXYGEN CONNECTOR SYSTEM

(76) Inventors: Darren A. Rubin, 3844 Chaucer Way, Land O'Lakes, FL (US) 34639; Howard Rubin, 3844 Chaucer Way, Land O'Lakes, FL (US) 34639

( * ) Notice: Subject to any disclaimer, the term of this patent is extended or adjusted under 35 U.S.C. 154(b) by 61 days.

(21) Appl. No.: 09/825,188

(22) Filed: Apr. 3, 2001

(51) Int. Cl.$^7$ ................................................ A62B 9/04
(52) U.S. Cl. .................. 128/202.27; 128/911; 128/912; 285/148.23; 285/386; 285/354; 285/38
(58) Field of Search ............................ 128/202.27, 911, 128/912; 285/148.23, 386, 38, 354

(56) References Cited

U.S. PATENT DOCUMENTS

| | | | | |
|---|---|---|---|---|
| 2,768,010 A | * | 10/1956 | Bird | 285/149.1 |
| 4,187,848 A | * | 2/1980 | Taylor | 604/243 |
| 4,844,409 A | * | 7/1989 | Lackler et al. | 251/149.9 |
| 4,991,820 A | * | 2/1991 | Kohn et al. | 251/149.5 |
| 5,226,898 A | * | 7/1993 | Gross | 604/243 |
| 5,466,173 A | * | 11/1995 | Down | 439/578 |
| 5,562,121 A | * | 10/1996 | Hodges et al. | 137/360 |
| 5,826,920 A | * | 10/1998 | Bartholomew | 285/305 |
| 5,901,987 A | * | 5/1999 | Godeau | 285/148.19 |
| 6,153,830 A | * | 11/2000 | Montena | 174/88 C |
| 6,309,543 B1 | * | 10/2001 | Fenton et al. | 210/232 |
| 6,347,643 B1 | * | 2/2002 | Cope et al. | 137/329.1 |

* cited by examiner

*Primary Examiner*—Aaron J. Lewis  
*Assistant Examiner*—Michael G. Mendoza  
(74) *Attorney, Agent, or Firm*—Edward P. Dutkiewicz

(57) ABSTRACT

An oxygen connector system for coupling an oxygen source to an oxygen tube comprises a source of oxygen. The source has an output orifice through which source oxygen is adapted to pass. The orifice has an inner bore and an outer surface. A flexible cylindrical elastomeric tube has a first input end and a second output end. The first input end is adapted to make a flush abutment with the source at the orifice. A generally cylindrical rigid connector has an exterior surface with a first region and a second region. An intermediate tapered region is provided between the first and second regions. The connector has a central generally cylindrical bore extending through the first and second ends forming an interior surface. The second end has a diameter slightly greater than that of the tube. A pair of stoppers are provided adjacent to the input end of the tube.

9 Claims, 4 Drawing Sheets

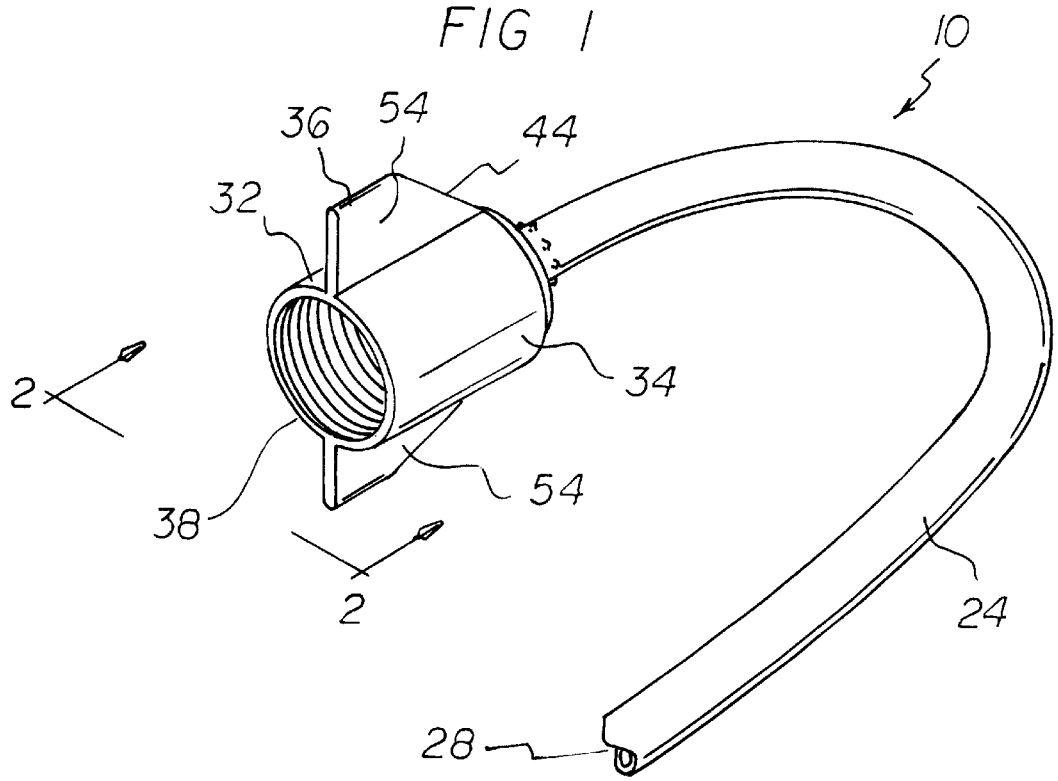
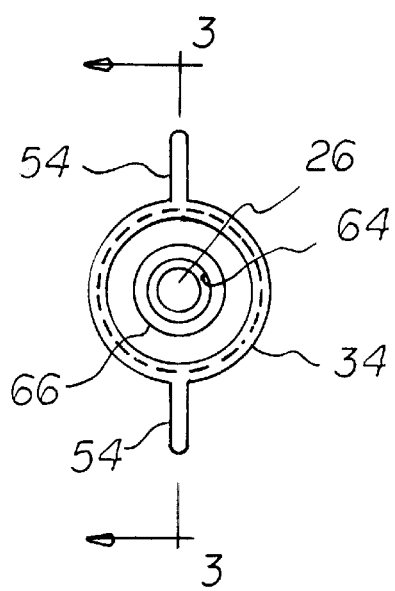

UNIVERSAL OXYGEN CONNECTOR SYSTEM

BACKGROUND OF THE INVENTION

1. Field of the Invention

The present invention relates to a universal oxygen connector system and more particularly pertains to coupling any of a plurality of different oxygen sources to an oxygen tube leading to any of a plurality of different oxygen utilizing devices.

2. Description of the Prior Art

The use of oxygen systems and connectors of known designs and configurations is known in the prior art. More specifically, oxygen systems and connectors of known designs and configurations previously devised and utilized for the purpose of coupling oxygen tubes with sources through known designs and configurations are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,446,863 to Rubin et al discloses a connector for inhalation therapy apparatus. U.S. Pat. No. 4,484,769 to Lacey discloses a non-rigid universal coupling for health related equipment. Lastly, U.S. Pat. No. 5,573,280 to Salter et al discloses a tubing endpiece and connector.

While these devices fulfill their respective, particular objectives and requirements, the aforementioned patents do not describe a universal oxygen connector system that allows for coupling any of a plurality of different oxygen sources to an oxygen tube leading to any of a plurality of different oxygen utilizing devices.

In this respect, the universal oxygen connector system according to the present invention substantially departs from the conventional concepts and designs of the prior art, and in doing so provides an apparatus primarily developed for the purpose of coupling any of a plurality of different oxygen sources to an oxygen tube leading to any of a plurality of different oxygen utilizing devices.

Therefore, it can be appreciated that there exists a continuing need for a new and improved universal oxygen connector system which can be used for coupling any of a plurality of different oxygen sources to an oxygen tube leading to any of a plurality of different oxygen utilizing devices. In this regard, the present invention substantially fulfills this need.

SUMMARY OF THE INVENTION

In view of the foregoing disadvantages inherent in the known types of oxygen systems and connectors of known designs and configurations now present in the prior art, the present invention provides an improved universal oxygen connector system. As such, the general purpose of the present invention, which will be described subsequently in greater detail, is to provide a new and improved universal oxygen connector system and method which has all the advantages of the prior art and none of the disadvantages.

To attain this, the present invention essentially comprises a first source of oxygen. The first source of oxygen has an enlarged output orifice. Source oxygen is adapted to pass through the enlarged output orifice. The output orifice has an inner bore. The output orifice also has an outer generally cylindrical surface. The outer cylindrical surface has male threads. Provided next is a flexible cylindrical elastomeric oxygen tube. The oxygen tube is of an extended length having a diameter. The oxygen tube has a first input end and a remote second output end. The first input end is adapted to make a flush abutment with the first source of oxygen at the output orifice. The second output end is adapted to attach to any of a plurality of oxygen utilizing devices. Next provided is a generally cylindrical rigid plastic connector. The connector has an exterior surface. The exterior surface has a first region of a first greater diameter at a first end. The exterior surface also has a second region of a second lesser diameter at a second end. An intermediated tapered region is provided between the first and second regions. The connector has a central generally cylindrical bore. The cylindrical bore extends through the first end and second end forming an interior surface. The first end has female threads on the interior surface. The first end is also adapted to couple with the male threads of the source of oxygen. The second end has a diameter slightly greater than that of the elastomeric oxygen tube. The second end is adapted to receive the oxygen tube. The interior surface within the second region has an annular recess. Further provided are a pair of flanges. The flanges protrude radially from the exterior surface of the connector. The flanges are located within the same plane on opposite sides of the connector. The flanges are adapted to assist a user in the coupling of the connector to the source of oxygen. Provided next are a plurality of enlarged stoppers. The stoppers extend radially from the tube at circumferentially spaced locations. The stoppers have a maximum diameter greater than the diameter of the second end of the connector. The stoppers are adapted to prevent the rubber tube from extending to a greater then desired distance into the connector. Even further provided is an elastomeric washer. The washer has a central aperture. The aperture has an internal diameter and an external diameter. The internal diameter is essentially equal to the diameter of the rubber tube. The washer is adapted to reside around the rubber tube within the bored out region of the connector. In this manner, the rubber tube is prevented from sliding out of the connector. The washer is located between the first input end of the tube and the stoppers. Next provided is an o-ring. The o-ring is fabricated of a lubricious material. The o-ring has an inner diameter and outer diameter. The inner diameter is essentially equal to that of the rubber tube. In this manner, a snug fit is provided between the connector and the rubber tube. The o-ring is located in the circular recess of the second region of the connector. Last provided is a second source of oxygen. The second source of oxygen has an output end of a reduced diameter with an axial bore. The second source also has an intermediate portion. The second source also has a base portion. All have a bore coaxial with the bore of the reduced output end. The reduced output end is adapted to couple within the first input end of the oxygen tube and allow the oxygen to pass from the source to the tube.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved universal oxygen connector system which has all of the advantages of the prior art oxygen systems and connectors of known designs and configurations and none of the disadvantages.

It is another object of the present invention to provide a new and improved universal oxygen connector system which may be easily and efficiently manufactured and marketed.

It is further object of the present invention to provide a new and improved universal oxygen connector system which is of durable and reliable constructions.

An even further object of the present invention is to provide a new and improved universal oxygen connector system which is susceptible of a low cost of manufacture with regard to both materials and labor, and which accordingly is then susceptible of low prices of sale to the consuming public, thereby making such universal oxygen connector system economically available to the buying public.

Even still another object of the present invention is to provide a universal oxygen connector system for coupling any of a plurality of different oxygen sources to an oxygen tube leading to any of a plurality of different oxygen utilizing devices.

Lastly, it is an object of the present invention to provide a new and improved oxygen connector system for coupling an oxygen source to an oxygen tube comprising a source of oxygen. The source has an output orifice through which source oxygen is adapted to pass. The orifice has an inner bore and an outer surface. A flexible cylindrical elastomeric tube has a first input end and a second output end. The first input end is adapted to make a flush abutment with the source at the orifice. A generally cylindrical rigid connector has an exterior surface with a first region and a second region. An intermediate tapered region is provided between the first and second regions. The connector has a central generally cylindrical bore extending through the first and second ends forming an interior surface. The second end has a diameter slightly greater than that of the tube. A pair of stoppers are provided adjacent to the input end of the tube.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the present invention.

FIG. 2 is an end view of the present invention along line 2—2 of FIG. 1.

The same reference numerals refer to the same parts throughout the various Figures.

DESCRIPTION OF THE PREFERRED EMBODIMENT

Figure 3:
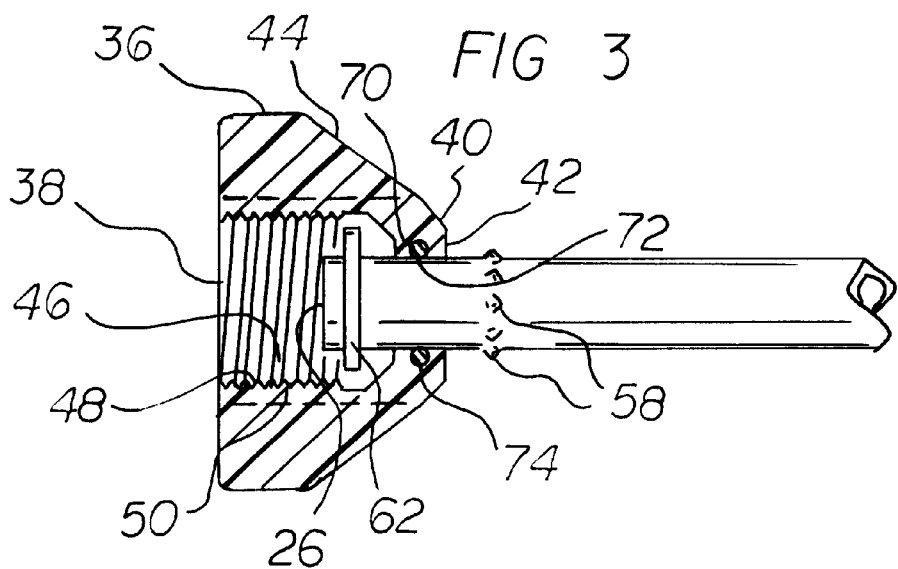
FIG. 3 is a cross sectional view of the connector coupled with the oxygen tube of the present invention.
Figure 4:
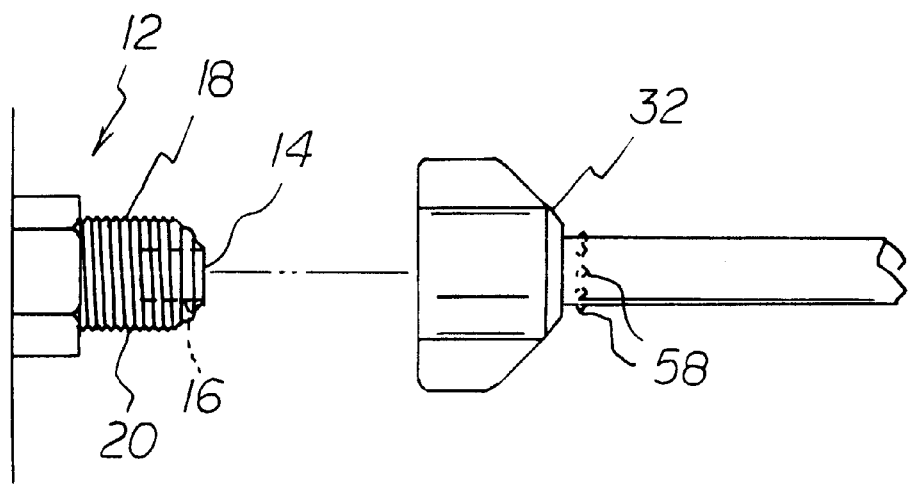
FIG. 4 is an exploded view of the connector and the first oxygen source of the present invention.
Figure 5:
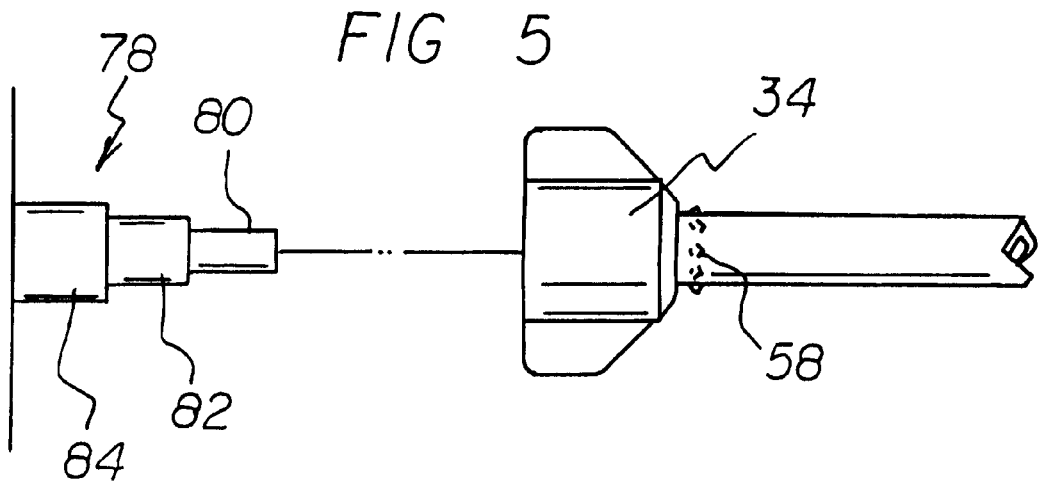
FIG. 5 is an exploded view of the connector and the second oxygen source of the present invention.

With reference now to the drawings, and in particular to FIG. 1 thereof, the preferred embodiment of the new and improved universal oxygen connector system embodying the principles and concepts of the present invention and generally designated by the reference numeral 10 will be described.

The present invention, the universal oxygen connector system 10 is comprised of a plurality of components. Such components in their broadest context include a source of oxygen, a flexible cylindrical elastomeric tube, a generally cylindrical rigid connector and a pair of spaced stoppers. Such components are individually configured and correlated with respect to each other so as to attain the desired objective.

Initially provided is a first source 12 of oxygen, normally a flow meter, as shown. The first source of oxygen has an enlarged output orifice 14. Source oxygen is adapted to pass through the enlarged output orifice. The output orifice has an inner bore 16. The output orifice also has an outer generally cylindrical surface 18. The outer cylindrical surface has male threads 20.

Provided next is a flexible cylindrical elastomeric oxygen tube 24. The oxygen tube is of an extended length having a diameter. The oxygen tube has a first input end 26 and a remote second output end 28. The first input end is adapted to make a flush abutment with the first source of oxygen at the output orifice. The second output end is adapted to attach to any of a plurality of oxygen utilizing devices, as for example, a mask, a nasal cannular, a nebulizer jar or the like.

Next provided is a generally cylindrical rigid plastic connector 32. The connector has an exterior surface 34. The exterior surface has a first region 36 of a first greater diameter at a first end 38. The exterior surface also has a second region 40 of a second lesser diameter at a second end 42. An intermediated tapered region 44 is provided between the first and second regions. The connector has a central generally cylindrical bore 46. The cylindrical bore extends through the first end and second end forming an interior surface 48. The first end has female threads 50 on the interior surface. The first end is also adapted to couple with the male threads of the source of oxygen. The second end has a diameter slightly greater than that of the elastomeric oxygen tube. The second end is adapted to receive the oxygen tube. The interior surface within the second region has an annular recess.

Further provided are a pair of flanges 54. The flanges protrude radially from the exterior surface of the connector. The flanges are located within the same plane on opposite sides of the connector. The flanges are adapted to assist a user in the coupling of the connector to the source of oxygen. The flanges create a surface that the user's fingers can push against to screw the connector onto the first oxygen source. The flanges are not the only method to achieve this objective. The flanges could be replaced with another type of grip on the exterior surface, such as rough exterior or indentations for the fingers.

Provided next are a plurality of enlarged stoppers 58. The stoppers extend radially from the tube at circumferentially spaced locations. The stoppers have a maximum diameter greater than the diameter of the second end of the connector. The stoppers are adapted to prevent the rubber tube from extending to a greater then desired distance into the connector.

Even further provided is an elastomeric washer 62. The washer has a central aperture 64. The aperture has an internal diameter and an external diameter 66. The internal diameter is essentially equal to the diameter of the rubber tube. The washer is adapted to reside around the rubber tube within the bored out region of the connector. In this manner, the rubber tube is prevented from sliding out of the connector. The washer is located between the first input end of the tube and the stoppers.

Next provided is an o-ring 70. The o-ring is fabricated of a lubricious material to facilitate rotation of the connector on the tube whereby the connector may be screwed onto the first oxygen source. The connector spins independently of the oxygen tubing. The connector thus screws onto the first oxygen source while the main tubing remains stationary. This prevents the main tubing from turning, coiling, or kinking. The o-ring is has an inner diameter 72 and outer diameter 74. The inner diameter is essentially equal to that of the rubber tube. In this manner, a snug fit is provided between the connector and the rubber tube. The o-ring is located in the circular recess of the second region of the connector.

Last provided is a second source 78 of oxygen. The second source of oxygen has an output end 80, formed as a nipple 80, of a reduced diameter with an axial bore. The second source also has an intermediate portion 82. The second source also has a base portion 84. All have a bore coaxial with the bore of the reduced output end. The reduced output end is adapted to couple through simple insertion into the first input end of the oxygen tube to thereby allow the oxygen to pass from the source to the tube. Sources of oxygen with a nipple at its output end, positionable in the input end of a tube, include tanks, nebulizers, some flow meters, and the like.

Figure 6:
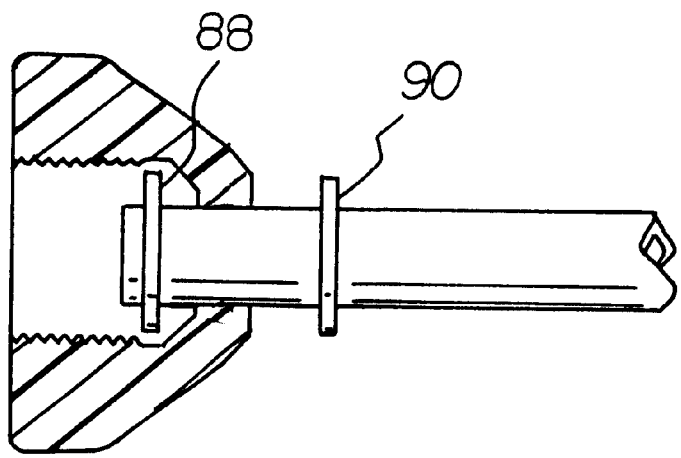
FIG. 6 is a cross sectional view of the connector coupled with an alternate embodiment of the oxygen tube stoppers.

An alternative embodiment of the invention is shown in FIG. 6. In such embodiment, essentially all of the components are the same as in the primary embodiment shown in FIGS. 1–5 except for the stoppers and the O-ring. In the primary embodiment, the stoppers are the raised dimples interiorly and the elastomeric washer exteriorly. In the alternate embodiment, the stoppers are elastomeric washers 88 and 90 both interiorly and exteriorly with the washers static bound on the tube. In addition, the O-ring of the primary embodiment is eliminated. Such O-ring is not mandatory but its use makes the connector easier to couple and uncouple with respect to the first oxygen source. The O-ring can allow the connector to spin more freely around the oxygen tube when twisting. It also allows for a snug fit between the connector and tube. It also allows for a superior more airtight seal when screwing the connector to the first oxygen source.

Figures 7, 8:
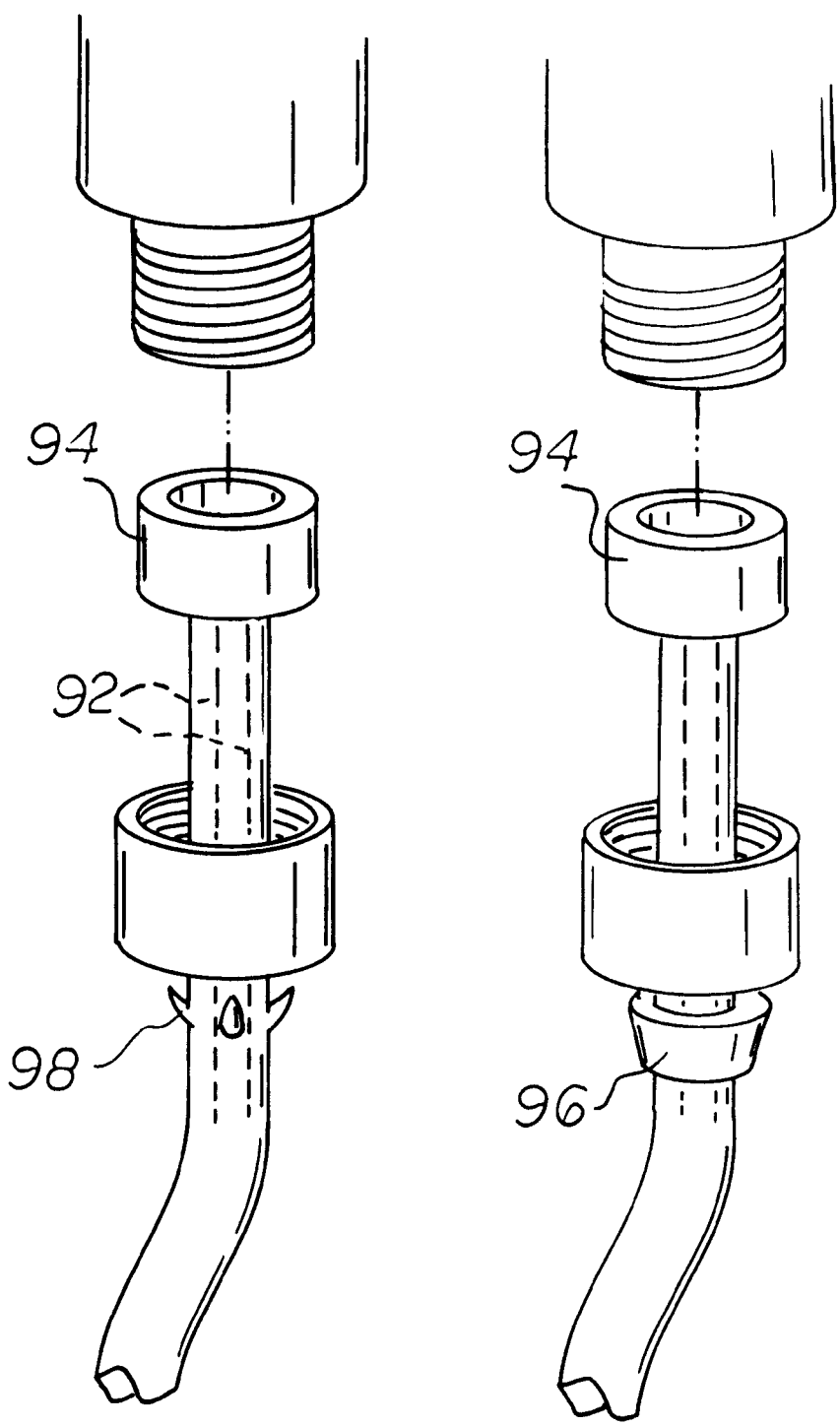
FIG. 7 is an exploded perspective illustration of an alternate embodiment of the invention.
FIG. 8 is an exploded perspective illustration of another alternate embodiment of the invention.

FIG. 7 is an exploded perspective illustration of an alternate embodiment of the invention. The interior stopper in this embodimdent, which was formed as washers 62 and 88 of the prior embodiments, is formed as an enlargement 94 at the input end of the tube. In addition, axial enlargements 92 are fabricated along interior lengths of the tube to abate kinking of the hose which might stop the flow of oxygen there through. The exterior stopper is formed as circumferentially spaced projections 98 angled toward the input end. This allows passage of the connector into its openable position as well as its retention in the location of FIG. 7 during operation and use.

The final embodiment is shown in FIG. 8. Such embodiment is similar to that of FIG. 8 except that the exterior stopper is formed as a single member 96 with a generally frusto-conical configuration.

Although the various components of the system could be fabricated of a wide variety of materials, the preferred materials are polyvinyl chloride (PVC) for the tube and, for the connector, polypropylene. The connector could also be fabricated of the same material as the tube for cost effectiveness. The connector may be rigid or semi-rigid.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A universal oxygen connector system for coupling any of a plurality of different oxygen sources to an oxygen tube leading to any of a plurality of different oxygen utilizing devices comprising, in combination;

a first source of oxygen having an enlarged output orifice through which source oxygen is adapted to pass, the output orifice having an inner bore and an outer generally cylindrical surface, with the outer cylindrical surface having male threads;

a flexible cylindrical elastomeric oxygen tube of an extended length having a diameter, a first input end and a remote second output end, the first input end making a flush abutment with the first source of oxygen at the output orifice, and the second output end adapted to attach to any of a plurality of oxygen utilizing devices;

a generally cylindrical rigid plastic connector with an exterior surface having a first region of a first greater diameter at a first end, a second region of a second lesser diameter at a second end and with an intermediated tapered region there between, the connector having a central generally cylindrical bore there through and extending through the first end and second end forming an interior surface, the first end having female threads on the interior surface and being adapted to couple with the male threads of the source of oxygen, the second end having a diameter slightly greater than that of the elastomeric oxygen tube and being adapted to receive there through the oxygen tube, the interior surface within the second region having an annular recess;

a pair of flanges radially protruded from the exterior surface of the connector, the flanges located within the same plane on opposite sides of the connector and adapted to assist a user in the coupling of the connector to the source of oxygen;

a plurality of enlarged stoppers extending radially from the tube at circumferentially spaced locations thereby giving the tube a maximum diameter greater than the diameter of the second end of the connector, the stoppers being adapted to prevent the tube from extending to a greater then desired distance into the connector;

an elastomeric washer having a central aperture with an internal diameter and having an external diameter, the internal diameter being essentially equal to the diameter of the tube, the washer being adapted to reside around the tube within the bored out region of the connector preventing the rubber tube from sliding out of the connector, the washer being located between the first input end of the tube and the stoppers;

an o-ring fabricated of a lubricious material having an inner diameter and outer diameter and with the inner diameter being essentially equal to that of the tube to ensure a snug fit between the connector and the tube, the o-ring being located in the circular recess of the second region of the connector with the washer to one side of the o-ring and the stoppers to the other side of the o-ring; and a second source of oxygen having an output end of a reduced diameter with an axial bore, the second source having an intermediate portion and a base portion, all with a bore coaxial with the bore of the reduced output end, the reduced output end being adapted to couple within the first input end of the oxygen tube and allow the oxygen to pass from the source to the tube.

2. An oxygen connector system for coupling an oxygen source to an oxygen tube comprising:

a source of oxygen having an enlarged output orifice through which source oxygen is adapted to pass, the output orifice having an inner bore and an outer generally cylindrical surface having male threads;

a flexible cylindrical elastomeric tube having a first input end and a remote second output end, the first input end making a flush abutment with the source of oxygen at the output orifice;

a generally cylindrical rigid connector with an exterior surface having a first region of a first greater diameter at a first end, a second region of a second lesser diameter at a second end and with an intermediate tapered region there between, the connector having a central generally cylindrical bore there through and extending through the first end and second end forming an interior surface, the first end having female threads on the interior surface and being adapted to couple with the male threads of the source of oxygen, the second end having a diameter slightly greater than that of the elastomeric oxygen tube;

an o-ring fabricated of a lubricious material having an inner diameter and outer diameter and with the inner diameter being essentially equal to that of the tube to ensure a snug fit between the connector and the rubber tube, the o-ring being located in a circular recess of the second region of the connector; and a pair of spaced stoppers adjacent to the input end of the tube with the space between the stoppers on opposite sides of the o-ring and the second end of the connector.

3. The universal oxygen connector system as set forth in claim 2 and further including a pair of flanges radially protruding from the exterior surface of the connector, the flanges located within the same plane on opposite sides of the connector and adapted to assist a user in the coupling of the connector to the source of oxygen.

4. The universal oxygen connector system as set forth in claim 2 further comprising a second source of oxygen which has an output end of a reduced diameter with an axial bore, the reduced output end being adapted to couple within the first input end of the tube and allow the oxygen to pass from the second source to the tube.

5. The universal oxygen connector system as set forth in claim 2 wherein one stopper includes raised dimples on the tube.

6. The universal oxygen connector system as set forth in claim 2 wherein one stopper is an elastomeric washer.

7. The universal oxygen connector system as set forth in claim 2 wherein the stoppers are a combination of raised dimples on the tube and an elastomeric washer.

8. The universal oxygen connector system as set forth in claim 2 wherein both stoppers are elastomeric washers.

9. The universal oxygen connector system as set forth in claim 2 wherein the connector spins independently of the oxygen tubing and screws onto the first oxygen source while the oxygen tubing remains stationary to thereby prevent the oxygen tubing from turning, coiling or kinking.

* * * * *